US007452377B2

(12) United States Patent
Watling et al.

(10) Patent No.: US 7,452,377 B2
(45) Date of Patent: Nov. 18, 2008

(54) BIOMEDICAL COMPOSITIONS

(75) Inventors: Jason Watling, Caulfield South (AU); Justine Leigh Jeffery, Mitcham (AU); Pathiraja Arachchillage Gunatillake, Mulgrave (AU); Timothy Charles Hughes, Lysterfield (AU)

(73) Assignee: Commonwealth Scientific and Industrial Reseach Organization

( * ) Notice: Subject to any disclaimer, the term of this patent is extended or adjusted under 35 U.S.C. 154(b) by 67 days.

(21) Appl. No.: 10/523,349

(22) PCT Filed: Jul. 30, 2003

(86) PCT No.: PCT/AU03/00958

§ 371 (c)(1), (2), (4) Date: Aug. 23, 2005

(87) PCT Pub. No.: WO2004/011529

PCT Pub. Date: Feb. 5, 2004

(65) Prior Publication Data

US 2006/0106458 A1 May 18, 2006

(30) Foreign Application Priority Data

Jul. 30, 2002 (AU) .............................. 2002950469

(51) Int. Cl.
*A61F 2/16* (2006.01)
(52) U.S. Cl. ..................... 623/6.11; 528/32; 528/43; 623/6.37; 623/6.56; 623/8; 623/23.72
(58) Field of Classification Search ................ None
See application file for complete search history.

(56) References Cited

U.S. PATENT DOCUMENTS

| 4,136,250 A | 1/1979 | Mueller et al. |
| 4,486,577 A | 12/1984 | Mueller et al. |
| 4,563,539 A | 1/1986 | Gornowicz |
| 4,605,712 A | 8/1986 | Mueller et al. |
| 4,616,045 A | 10/1986 | Upchurch |
| 4,852,969 A | 8/1989 | Babirad et al. |
| 5,079,319 A | 1/1992 | Mueller |
| 5,116,369 A * | 5/1992 | Kushibiki et al. .......... 623/6.56 |
| 5,233,007 A | 8/1993 | Yang |
| 5,236,970 A | 8/1993 | Christ |
| 5,246,979 A * | 9/1993 | Lutz et al. .................... 522/42 |
| 5,278,258 A | 1/1994 | Gerace |
| 5,346,946 A | 9/1994 | Yokoyama |
| 5,376,694 A | 12/1994 | Christ |
| 5,391,590 A | 2/1995 | Gerace |
| 5,411,553 A | 5/1995 | Gerace |
| 5,420,213 A | 5/1995 | Yang |
| 5,444,106 A | 8/1995 | Zhou |
| 5,476,515 A | 12/1995 | Kelman et al. |
| 5,494,946 A | 2/1996 | Christ |
| 5,556,383 A | 9/1996 | Wang et al. |
| 5,610,257 A | 3/1997 | Richard et al. |
| 5,647,409 A | 7/1997 | Christ |
| 5,661,195 A | 8/1997 | Christ |
| 5,772,667 A | 6/1998 | Blake |
| 5,869,549 A | 2/1999 | Christ |
| 5,977,282 A | 11/1999 | Ebbrecht et al. |
| 5,981,615 A | 11/1999 | Meijs et al. |
| 6,066,172 A | 5/2000 | Huo |
| 6,277,147 B1 | 8/2001 | Christ |
| 6,361,561 B1 | 3/2002 | Huo |
| 6,399,734 B1 | 6/2002 | Hodd |
| 6,663,668 B1 | 12/2003 | Chaouk et al. |
| 6,737,496 B2 * | 5/2004 | Hodd et al. .................... 528/32 |
| 7,348,022 B1 | 3/2008 | Clayton et al. |
| 2002/0082691 A1 | 6/2002 | Christ et al. |
| 2003/0092866 A1 * | 5/2003 | Qureshi et al. ................. 528/27 |
| 2005/0004255 A1 | 1/2005 | Clayton et al. |
| 2005/0228120 A1 | 10/2005 | Hughes et al. |

FOREIGN PATENT DOCUMENTS

| EP | 0293560 | 12/1988 |
| EP | 0335312 | 10/1989 |
| EP | 0578087 | 1/1994 |
| EP | 1176454 A1 | 1/2002 |
| JP | 2002-128829 | 5/2002 |
| WO | WO 93/21245 | 10/1993 |
| WO | WO 00/22459 | 4/2000 |
| WO | WO 00/22460 | 4/2000 |
| WO | WO 01/08603 | 2/2001 |
| WO | WO 01/17570 | 3/2001 |
| WO | WO 01/76651 | 10/2001 |
| WO | WO 01/81075 | 11/2001 |

OTHER PUBLICATIONS

Zelentsova, N.V., Zelentsov, S.V. Abadie, M.J.M and Makareeva, N "Photochemical crosslinking of the low molecular weight vinyl containing polysiloxanes with organic azides," Phobiology 20002.
Fisher, R.F. et al; The elastic constants of the human lens; J. Physiology, Jan. 29, 2008; 1971; 212; pp. 147-180.
Heys, K.R. et al; Massive increase in the stiffness of the human lens nucleus with age: the basis for presbyopia?; Molecular Vision; Nov. 17, 2004; vol. 10; pp. 956-963.
Phan-Thien Nhan et al; Micro-Fourier rheometer: Inertial effects; Rheol Acta; 1996; vol. 35; pp. 410-416.
Schachar, R.A. et al; Viscoelastic shear properties of the fresh porcine lens; Br J Ophthalmol; 2007; vol. 91; pp. 366-368.
Weeber, H.A. et al; Dynamic mechanical properties of human lenses; Experimental Eye Research; 2005; vol. 80; pp. 425-434.
Ziebarth; N.M. et al; Atomic force microscopy measurements of lens elasticity in monkey eyes; Molecular Vision; 2007; vol. 13; pp. 504-510.
Modulus of Elasticity; Glossary of Materials Testing Terms; Instron; web site as of Apr. 10, 2008.

* cited by examiner

*Primary Examiner*—Marc S Zimmer
(74) *Attorney, Agent, or Firm*—Andrus, Sceales, Starke & Sawall, LLP

(57) ABSTRACT

The invention provides in one form a macromonomer comprising a polysiloxane copolymer having a backbone structure derived from siloxane monomer units that are substituted or unsubstituted arylsiloxanes, arylalkylsiloxanes, alky(alkyl)siloxanes of the general formula —$R_1R_2SiO$— and wherein the terminal groups of the copolymer backbone include crosslinkable groups and wherein pendent from the backbone are at least two crosslinkable groups. The macromonomer may be cured in vivo by ultraviolet or visible light. The invention includes intraocular lenses formed by such macromonomers.

15 Claims, 1 Drawing Sheet

BIOMEDICAL COMPOSITIONS

CROSS-REFERENCE TO RELATED APPLICATIONS

Figure 1:
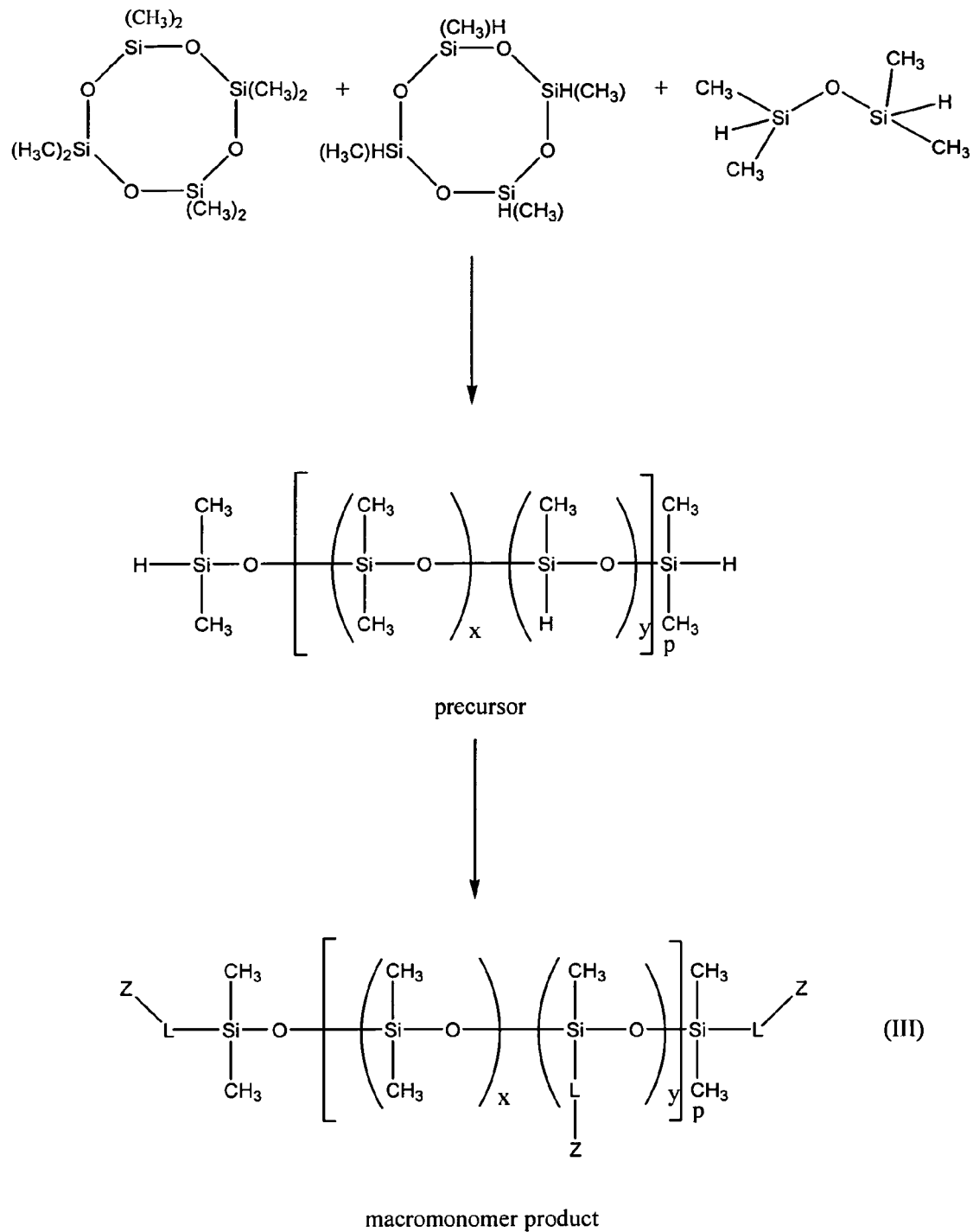

This application is the U.S. national stage application of International Application PCT/AU2003/000958, filed 30 Jul. 2003, which international application was published on 5 Feb. 2004, as International Publication WO2004/011529 in the English language. The International Application claims priority of Australian Patent Application 2002950469, filed 30 Jul. 2002.

TECHNICAL FIELD OF THE INVENTION

This invention relates to ethylenically unsaturated macromonomers that are suitable for use as precursors for polymers that have biomedical applications, including in particular as injectable precursors for prostheses and intraocular lenses (IOLs).

BACKGROUND OF THE INVENTION

Synthetic materials for prostheses and similar applications are in demand. In one application, it is known that, as adults age, the accommodative power of the eye decreases leading to the onset of presbyopia. This age-related decrease in accommodative power is believed to be caused by a decrease in the elasticity of the lens material. This decrease is probably caused by denaturation and dehydration of the lens material. Thus the loss of accommodation results from a change in elasticity rather than a decrease in the action of the ciliary muscles. The replacement of the original lens with a synthetic polymer having the elasticity equivalent to the lens of a young adult offers the prospect of being able to use a surgical procedure to replace the need for glasses to correct presbyopia.

The use of polymeric prostheses and biomedical mouldings has grown rapidly in recent times. Such mouldings may be used for contact lenses or for specific ophthalmic purposes. For example, they may be used for intraocular lenses and eye bandages. They may also be used for surgical mouldings such as heart valves and artificial arteries. Other applications include wound dressings, biomedical adhesives and tissue scaffolds. Use in drug delivery is a further application.

Diseases of the lens material of the eye are often in the form of cataracts. The ideal cataract procedure is considered to be one where the lens capsule bag is maintained with the cataractous lens material removed through a small opening in the capsule. The residual epithelial cells of the lens are removed chemically and/or with ultrasound or lasers followed by aspiration. A biocompatible artificial lens (also called an "IOL", such as known PMMA lenses) with appropriate optical clarity, refractive index and mechanical properties is then inserted into the capsular bag to restore the qualities of the original crystalline lens. The desired refractive index is about 1.41. For many years most of these lenses have been made of poly(methylmethacrylate) (PMMA), a material with good optical characteristics and compatibility with tissues in the eye. However, PMMA is a very rigid material (and therefore non-accommodating) and the incision must be made big enough, at least 5-6 mm, for implantation of the lens. With improved devices for removal of the natural lens that require only small (3-4 mm) incision, there is a need for lenses which are foldable.

There have also been recent advances in methods of inserting intraocular lens. For example, U.S. Pat. No. 5,772,667 assigned to Pharmacia Lovision Inc., discloses an intraocular lens injector. This device compresses an IOL by rolling the lens into a tight spiral. The device then injects the compressed IOL through a relatively small incision in the eye, approximately 2-3 millimeters in length, resulting from a phacoemulsification procedure. The IOL is inserted into a receiving channel of the injector device in an uncompressed state and is urged into a cylindrical passageway. As the IOL advances into the cylindrical passageway, the IOL rolls upon itself into a tightly rolled spiral within the confines of the cylindrical passageway. An insertion rod is then inserted into an open end of the cylindrical passageway and advances the compressed IOL down the passageway. As the IOL exits the passageway and enters the eye, the IOL will expand back to its uncompressed state. Although these IOLs offer significant advances the implantation of these types of non-accommodating IOLs still requires the patient to use spectacle correction for reading.

To avoid the need for such injection devices and to also overcome the limitation of conventional IOLs (namely, requiring reading spectacles), it has been proposed that intraocular lenses be formed in situ after being injected as a liquid flowable form into the lens capsule bag. However, while this concept is attractive in that smaller incisions would be required, it raises further difficulties in that further chemical reactions are required to cure the injectable material and these are required to be not harmful to the patient. It is also a requirement that the chemical reactions can take place over a relatively short time under mild reaction conditions. It is desirable that the reaction is also not significantly inhibited by oxygen. A still further requirement is that no by-products or residues are produced that may have an adverse biological effect on the patient.

In our co-pending international patent application PCT/AU00/00915 references relating to ethylenically unsaturated macromonomers are discussed and an invention relating to novel macromonomers suitable for use as injectable precursors for intraocular lenses are described. In particular, there is described an ethylenically unsaturated macromonomer comprising units of formula:

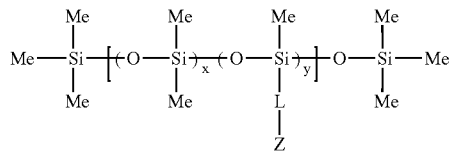

where L is a linker group

Z is an ethylenically unsaturated free radical polymerisable group y is $\geq 2$ x is $\geq 5$ and wherein the ethylenically unsaturated groups are provided by (meth)acrylate or (meth)acrylamide moieties. The linker group, L, functions as a spacing group which allows the required ethylenic unsaturated group Z to be attached to the copolymer backbone. It may be a linear, branched or cyclic hydrocarbyl chain. It may contain hetero atoms as well as carbonyl and other substituted atoms. The entire contents of that specification (published as WO 01/08603) is incorporated herein by reference.

Although the macromonomers described in that specification meet many of the requirements for the preferred end use application we have now found a new class of macromonomer that provides accommodating intraocular lenses with superior properties.

SUMMARY OF THE INVENTION

This invention provides a macromonomer comprising a polysiloxane copolymer having a backbone structure derived from siloxane monomer units that are substituted or unsubstituted arylsiloxanes, arylalkysiloxanes, alky(alkyl)siloxanes of the general formula —$R_1R_2SiO$— and wherein the terminal groups of the copolymer backbone include crosslinkable groups.

In one embodiment, there is provided an ethylenically unsaturated macromonomer comprising a polysiloxane copolymer having a backbone structure derived from siloxane monomer units that are substituted or unsubstituted arylsiloxanes, arylalkysiloxanes, alky(alkyl)siloxanes of the general formula —$R_1R_2SiO$— and wherein the terminal groups of the copolymer backbone include ethylenically unsaturated crosslinkable groups and wherein pendent from the backbone is at least one ethylenically unsaturated crosslinkable group.

Preferably the ethylenically unsaturated groups are (meth) acryl groups.

Preferably the (meth)acryl groups are (meth)acrylamide groups.

In another form the present invention provides a macromonomer of general formula:

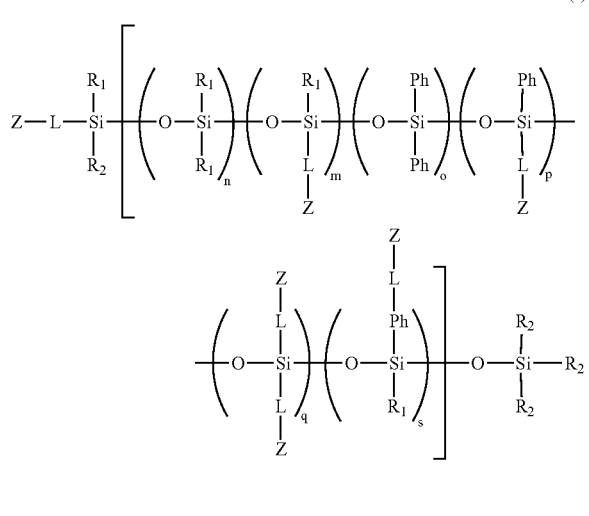

(I)

wherein
L is a spacer group;
Z is a crosslinkable group, such as an ethylenically unsaturated free radical polymerisable group;
each $R_1$ is independently $C_1$ to $C_6$ alkyl or perfluorinated $C_1$ to $C_6$ alkyl;
each $R_2$ is independently an $R_1$ or L-Z group;
the molar percentage of:
n is from 0 to 100%;
m is from 0 to 10%;
o is from 0 to 50%;
p is from 0 to 2%;
q is from 0 to 2%;
s is from 0 to 2%.
Preferably the molecular weight of the macromonomer is more than 3,000, preferably more than 20,000. Preferably, o+p=0 when L or $R_1$ contain fluorine. Thus, in this embodiment, the macromonomer does not have both fluorinated alkyl groups and phenyl groups on the siloxane backbone.
Preferably, n is from 50 up to but not including 100%.
Preferably, m is from 0 to 5%.
Preferably, o is from 0 to 25%.
$R_1$ is preferably —$CH_3$. Where $R_1$ is perfluorinated $C_1$-$C_6$ alkyl, it will usually be a $C_3$-$C_6$ perfluorinated alkyl.
In many useful embodiments, p, q and s are 0% and o is 0 to 10%.
Preferably, both terminal Si residues are bound to identical or different L-Z groups.

In a preferred embodiment, the macromonomers have 100 to 6,000 —Si—O-monomeric units each, more preferably 700 to 3,000, and more preferably 1,300 to 2,200.

The macromonomers of the invention are preferably random copolymers. However block type copolymers and alternating copolymers also fall within the scope of the present invention.

The spacer or linker group, L, functions as a group which allows the required ethylenlic unsaturated group Z to be attached to the copolymer backbone. It may be a linear, branched or cyclic hydrocarbon chain. It may contain hetero atoms as well as carbonyl and other substituted atoms.

Crosslinkable groups, Z, include (meth)acryl, isocyanate and epoxy groups. The term (meth)acryl group includes acryl or substituted acryl, such as methacryl, moieties attached through a variety of linkages including ester, amide and urethane linkages, or functional analogues of (meth)acryl capable of undergoing crosslinking reactions with a photo-initiator. Examples of functional acryl groups include acrylamidoalkyl, methacrylamidoalkyl, acryloxyalkyl and methacryloxyalkyl.

As will be appreciated, in the general Formula I, the $R_1$, L and Z groups may vary with the alternatives given in the above definitions. For example, as one skilled in the art would appreciate, the macromonomer may be synthesised by substituting two or more different -L-Z groups on to the backbone. Accordingly, the invention does not require that every L or Z be identical in a given macromonomer.

In another form, the invention provides a macromonomer of general formula:

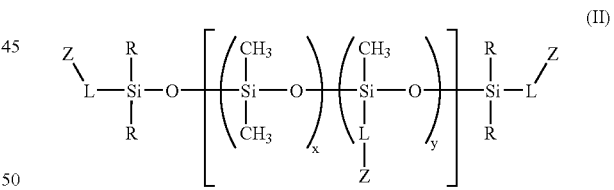

(II)

wherein R is $R_1$ or L-Z as defined above and L and Z are as defined above and x is from 90 to 100%, y is from 1 to 10%, and has a molecular weight of 3,000, preferably 20,000, to 300,000. In a preferred embodiment, the macromonomers have 100 to 6,000 —Si—O-monomeric units each, more preferably 700 to 3,000, and more preferably 1,300 to 2,200.

The invention also provides a method of preparing a macromonomer of Formula I or Formula II wherein hydride terminated groups, preferably tetramethyldisiloxane, are used as intermediate reactants with cyclic oligomers.

Macromonomers of the present invention can be made with a specific gravity of less than 1, although this is not required. In some applications, a specific gravity of more than 1 is desirable to prevent the material from floating when applied to a solution consisting essentially of water, for example, an intraocular lens formed in situ. The issue of the macromonomer floating in an intraocular lens application may also be overcome by the use of an MCV (mini-capsulorhexis valve) when injecting the macromonomer into the eye. The MCV device comprises a flexible discoid flap-valve member attached to a flexible retainer member, the device serving to seal a capsulorhexis opening created during ocular interventions.

Macromonomers according to this invention also include polymerisable side groups. Without being bound by any theory or mode of action, it is believed that the side groups (or crosslinkable groups) increase cross-linking between macromonomers, (ie, increase the probability of each polymer chain being incorporated into the polymer network) which results in lower "extractables". Extractable or unbound macromonomers are undesirable, especially in in viva applications. For example, in an intraocular lens application, unreacted macromonomers are extractables which, if not removed from the vicinity of the lens, may cause deleterious or otherwise undesirable side effects. Locating the ethylenically unsaturated groups terminally is considered advantageous as it assists in reducing extractables while retaining good viscoelastic properties in the cured or crosslinked polymer.

In optimising macromonomers for accommodating intraocular lens applications according to the present invention, it has been discovered, surprisingly, that two key variables alter a number of the properties or characteristics which are required of an intraocular lens. These two variables are the cross-link density (ie, the number of cross-linkable or polymerisable side groups and terminal groups) and the molecular weight of the macromonomer. Without being bound by any theory or mode of action, it is believed that four key characteristics of a macromonomer for an intraocular lens application are the modulus of the intraocular lens once cured, the composition's cure kinetics (which may also be assessed as the degree of incorporation of the composition into the lens of the cornea), the viscosity of the uncured composition (which relates to the ease of injectability) and the proportion of extractables after curing. The amount of extractables is directly affected by both variables as decreased cross-link density is generally associated with an increased amount of extractables (as described above) but this can be counteracted by increased molecular weight macromonomers which due to their overall longer length possess more crosslinkable groups per chain at constant cross-link density, and so therefore each macromonomer has a greater probability of being incorporated into the bulk without resulting in a higher modulus. The main limitation on cross-linking density is to keep the modulus of the cured intraocular lens sufficiently low so that it can be manipulated by the ciliary muscles (ie, so that it is not too rigid). The balancing consideration for cross-link density is that greater cross-link density improves the cure kinetics and also reduces the level of extractables. It is desirable to produce a macromolecule that possesses the lowest number of crosslinkable groups per chain in order to obtain the maximum elasticity of the cured material, but that still contains sufficient crosslinkable groups such that it can be cured into a single mass. In the case of molecular weight, as mentioned above, higher molecular weight decreases extractables but the balancing consideration is that higher molecular weight macromonomers increase viscosity and therefore decrease ease of injectability. As a result, compositions according to the invention must balance these requirements and this is achieved by the invention in a manner not previously described. Following this approach, it has been surprisingly found that the addition of terminal polymerisable groups assists in better balancing these competing considerations.

Another advantage of the composition of the invention is the ability to substitute different side chains on the siloxane monomer repeating unit which alters the refractive index of the cured composition when used in a lens application. The normal refractive index of a polysiloxane composition according to the invention is about 1.41, roughly corresponding to a healthy young crystalline lens. Di-aromatic substitutions along the backbone can increase the refractive index up to about 1.46 where that is useful to correct the refractive error (hypermetropia) of the eye being treated. Alternatively, perfluorinated alkyl substitutions on the siloxane backbone can reduce the refractive index to about 1.35 for the opposite correction (myopia). The availability of higher and lower indices are an advantage because using a lens with a refractive index higher (or lower) than that of the natural lens allows single vision refractive errors to be corrected in addition to presbyopia. The siloxane unit may have both a phenyl (and/or perfluorinated alkyl) and crosslinkable group as outlined in Formula I.

Accordingly, in another form of the invention, there is provided a composition which is curable into an accommodating intraocular lens vivo. The composition can be injected into the lens capsule and then cured by visible or ultraviolet light. The lens once formed has a sufficiently low modulus that the ciliary muscles controlling the zonules can still adjust the crystalline lens shape in the usual way and the lens can accommodate to these movements in the ciliary body. In particular, the composition comprises ethylenically unsaturated groups, which are more preferably acryl or methacryl groups. (Meth)acrylamide groups are particularly preferred.

In preferred forms of the invention, the molecular weight of the macromonomer is between 50,000 and 250,000, preferably 100,000 to 160,000, and the elasticity modulus is desirably between 0.1 and 5 kPa, as measured by a Micro Fourier Rheometer (see below).

DETAILED DESCRIPTION OF THE INVENTION

The invention will now be further described by reference to non-limiting examples. FIG. 1 shows a general scheme of reaction for synthesis of macromonomers of the invention.

The macromonomers of the present invention offer the advantage that they contain more crosslinkable or reactable groups per polymer chain than some of the prior art polymers but also exhibit the desired mechanical and optical properties, particularly when used as an injectable precursor for an intraocular lens. The macromonomers are also applicable in a number of other areas, including breast implants, soft tissue replacements, soft tissue filling agents or vitreous/aqueous humor replacement. These applications make use of the characteristics of being readily handled prior to cure, minimising extractables while being curable in vivo and being able to predetermine and vary the elasticity, or E, modulus.

The macromonomers set out in the above scheme of reaction as well as in Formula I are preferably random copolymers. However block type copolymers also fall within the scope of the present invention.

The macromonomers of this invention may be polymerised by free radical polymerisation to form crosslinked or cured polymers. The mechanical and optical properties of the polymers are preferably matched to those of the natural biological material. In the case of lens material for the eye the refractive index should be close to 1.41. One measure of the mechanical properties is the flexibility of such a polymer as measured by its elasticity modulus (as measured by its E modulus). The polymer shear modulus is a related property that may be measured also. Both can be measured as the force required to deform a product, such as a lens, formed by the polymer by measuring stress against strain. This shear modulus of the polymer of the invention may be measured by a Micro Fourier Rheometer. A Bohlin controlled stress rheometer may also be used. For a lens application of this invention, the shear modulus measured by a Micro Fourier Rheometer in this way is preferably in the range 0.01-100 kPa, preferably 0.1-10 kPa and most preferably 0.1-5 kPa. The E modulus is influenced by the number of ethylenically unsaturated groups per macromonomer and also average spacing (ie the relative proportion of ethylenically unsaturated monomer) of the ethylenically unsaturated groups. Generally as the number of ethylenically unsaturated groups per macromonomer molecule decreases or the average spacing between ethylenically unsaturated groups increases (as a result of the monomeric proportions) the elasticity of the cured polymer decreases.

The crosslinking process is preferably carried out in such a way that the resulting network polymer is free or essentially free from undesired constituents. A particular undesired constituent is starting macromonomers that have had none of their polymerisable groups incorporated into the network and as such are potentially extractable from the resulting network polymer after cure. The macromonomer is preferably used without the addition of a comonomer although a comonomer may be included. While generally the compositions of the present invention do not usually involve the use of other macromonomers, these may be optionally included. This can be an advantage when the refractive index or viscosity needs to be adjusted. Preferably the compositions comprise at least 50%, more preferably at least 80%, by weight of macromonomers as defined in the present invention.

In the case of photo cross-linking, it is expedient to add an initiator which is capable of initiating free-radical crosslinking. It is preferred that the initiators are activated by light in the visible spectrum rather than UV light as this enables the use of frequencies to cure the polymer that are not harmful to the eye or retina. Examples thereof are known to the person skilled in the art; suitable photoinitiators which may be mentioned specifically are benzoins, such as benzoin, benzoin ethers, such as benzoin methyl ether, benzoin ethyl ether, benzoin isopropyl ether and benzoin phenyl ether, and benzoin acetate; acetophenones, such as acetophenone, 2,2-dimethoxyacetophenone and 1,1-dichloroacetophenone; benzil, benzil ketals, such as benzil dimethyl ketal and benzil diethyl ketal, camphorquinone, anthraquinones, such as 2-methylanthraquinone, 2-ethylanthraquinone, 2-tert-butylanthraquinone, 1-chloroanthraquinone and 2-amylanthraquinone; furthermore. triphenylphosphine, benzoylphosphine oxides, for example 2,4,6-trimethylbenzoyl-diphenylphosphine oxide; Eosin homologues such as Eosin Y, Phloxine, Rose Bengal and Erytlrosin; benzophenones, such as benzophenone and 4,4'-bis(N,N'-dimethylamino) benzophenone; thioxanthones and xanthenes; acridine derivatives; phenazine derivatives; quinoxaline derivatives and 1-phenyl-1,2-propanedione 2-O-benzoyl oxime; 1-aminophenyl ketones and 1-hydroxyphenyl ketones, such as 1-hydroxycyclohexylphenyl ketone, phenyl 1-hydroxyisopropyl ketone, 4-isopropylphenyl 1-hydroxyisopropyl 1-hydroxyisopropyl ketone, 2-hydroxy-1-[4-2(-hydroxyethoxy) phenyl]-2-methylpropan-1-one, 1-phenyl-2-hydroxy-2-methylpropan-1-one, and 2,2-dimethoxy-1,2-diphenylethanone, all of which are known compounds.

Particularly suitable photoinitiators, which are usually used with visible light sources are IRGACURE®819, Eosin homologues such as Rose Bengal, Eosin B, and fluorones such as H-Nu 470, H-Nu635 and derivatives.

Particularly suitable photoinitiators, which are usually used with UV lamps as light sources, are acetophenones, such as 2,2-dialkoxybenzophenones and hydroxyphenyl ketones, in particular the initiators known under the trade names IRGACURE®651 and IRGACURE®184. A particularly preferred photoinitiator is IRGACURE®819.

The photoinitiators are added in effective amounts, expediently in amounts from about 0.05 to about 2.0% by weight, in particular from 0.1 to 0.5% by weight, based on the total amount of cross-linkble macromonomer. In addition the photoinitiator can be incorporated/grafted onto the polymer backbone. Such immobilisation of the polymer has the advantage of reducing the availability of photoinitiator residues for extraction post cure.

The resultant cross-linkable macromonomer can be introduced into a mould using methods known per se, such as, in particular, conventional metering, for example dropwise. Alternatively, the macromonomers may be cured in situ, as for example in the case of an injectable lens. In this case the macromonomer is cured or crosslinked in the lens capsule after injection.

The cross-linkable macromonomers which are suitable in accordance with the invention can be crosslinked by irradiation with ionising or actinic radiation, for example electron beams, X-rays, UV or VIS light, ie electromagnetic radiation or particle radiation having a wavelength in the range from about 280 to 750 nm. Also suitable are UV lamps, He/Dc, argon ion or nitrogen or metal vapour or NdYAG laser beams with multiplied frequency. It is known to the person skilled in the art that each selected light source requires selection and, if necessary, sensitisation of the suitable photoinitiator. It has been recognised that in most cases the depth of penetration of the radiation into the cross-linkable macromonomer and the rate of curing are in direct correlation with the absorption coefficient and concentration of the photoinitiator. Curing might also be achieved by employing one or more of these methods, eg, heat and light.

If desired, the crosslinking can also be initiated thermally. It should be emphasised that the crosslinking can take place in a very short time in accordance with the invention, for example, in less than twelve hours, preferably in less than hour, more preferably in less than 30 minutes. It will be appreciated that while the macromonomers of this invention may be used alone to form the lenses and other biocompatible materials, other materials may also be present. For example, diluents may be present as well as other monomers including other macromonomers. Other additives to the macromonomer precursor, which may be free or grafted onto the polymer backbone, can include ultraviolet absorbers or compounds that inhibit or kill the cells associated with PCO (Posterior Capsule Opacification). When used as an injectable material the macromonomers should have a viscosity in the range 1,000-150,000 cS and more preferably 1,000-60,000 cS at 25° C. Instruments such as the Brookfield rheometer or the Bohlin controlled stress rheometer may be conveniently used for measurement.

The polysiloxane copolymers of the present invention may be prepared as set out below. The synthesis uses hydride terminated groups (from a methyldisiloxane, such as tetramethyldisiloxane) rather than tetramethyldivinylsiloxane groups as used in U.S. Pat. No. 6,066,172. Disilaxane with fewer methyl groups may be used if greater degrees of functionalisation are required. This enables a far greater range of polymerisable end groups to be incorporated. For example acrylamide, methacrylate, or acrylate groups may be incorporated and these are far more reactive than the vinyl groups as outlined in U.S. Pat. No. 6,066,172. The cure times are typically significantly reduced when compared to macromonomers with vinyl groups. In the present invention (meth)acryl groups are the preferred ethylenically unsaturated groups. This allows, especially with acrylamide groups, the use of significantly less cytotoxic photoinitiators. The use of tetramethyldisiloxane as the end group in synthesis of the polymer precursor (macromonomer) offers significant advantages by utilising the hydride groups. Crosslinkable groups can be added to the hydride using allyl-precursors, such as allyl (meth)acrylate and allyl isocyanate, in methods known to those skilled in the art. In this way, other commonly used crosslinkable groups (such as epoxy or isocyanate) can be incorporated into the macromonomer in place of, or in addition to, (meth)acrylate groups. As such, the synthesis can provide crosslinkable macromonomers that do not require ethylenic unsaturation to be present.

The general reaction scheme for synthesis of macromonomers according to one embodiment of the invention is set out in FIG. 1. As can be seen from FIG. 1, the octamethylcyclotetrasiloxane forms the non-reactive monomeric unit of the siloxane macromonomer, the tetramethylcyclotetrasiloxane forms the monomeric unit with the reactable hydride group, and tetramethyldisiloxane (although disiloxane with fewer methyl substitutions may be used for additional terminal crosslinkable groups—and other substitutions may also be used) forms the terminal monomers of the siloxane chains, again with a reactive hydride group at each end. The ratio of x and y in the macromonomer precursor (see Formula III in FIG. 1) is determined by the proportions of reagents used. In the following step, some or all of the hydride groups are reacted to substitute side or terminal groups in manners known to one skilled in the art. In particular, allyl groups can be reacted with the hydride in the presence of a catalyst (such as a platinum catalyst). Depending upon the stoichiometry, some or all of the hydride groups will be replaced with the -L-Z side/terminal group to form a macroanonomer according to the invention.

A more generaised form of the invention is shown in Formula II above. Moreover, in this form of the invention, it will be appreciated by one skilled in the art that not all hydride groups may be reacted and thus the invention includes macromonomers of general Formula II which further include some monomeric units of Formula SiH $CH_3O$. Also, depending upon the end groups used, it is possible for the R groups in Formula II to include -L-Z. Accordingly, the end groups of a copolymer chain may have in total two or more polymerisable groups. While R may be any of the moieties defined, a methyl group is preferred as it is the most commonly used and readily available siloxane feedstock available.

The monomer unit may also have two crosslinkable groups as outlined in structure (I). The siloxane monomer unit may also contain aromatic groups that include a crosslinkable group, such as styrenic groups.

The preferred molecular weight range of the macromonomers is from 3000 up to 400,000 AMUs, preferably 20,000 to 350,000. Molecular weights above about 160,000 are relatively viscous, which makes injectability (particularly in the delicate application in the capsular bag) difficult. However, higher molecular weight macromonomers are suitable for use with injection mechanisms that are mechanically assisted to generate the necessary pressures to inject more viscous solution. At the other end of the range, macromonomers with molecular weights below about 3,000 are generally too fluid to prevent leakage from the capsular bag in use. The preferred viscosity range is 1000 cP to 60,000 cP. The preferred molecular weight range for manual injection is 60,000 to 160,000 AMUs and especially 100,000 to 160,000 AMU.

With reference to Formula I, the total number of monomer units is in the range 30 to 6000 but preferably 700 to 2000.

The dialkyl siloxane component will generally make up by far the greatest portion of the material. In non-diphenyl containing formulations, n will be in the range of 90-100% (molar percent) and especially 98-100%. In diphenyl based applications the value of n+o will range from 90-100% and especially 95-100%.

For the alkylsiloxane unit bearing the crosslinkable group, m will have a value of from 0 to 10%, preferably 0 to 5%, more preferably 0 to 2% and especially 0 to 1%. Values higher than about 2% for m are more likely to produce materials that have too high modulus for many applications.

The other crosslinkable groups specified, (m, p, q, s) will preferably be present such that total molar percentage of m+p+q+s<=2% and especially <=1%, of the macromonomer. As the value of the total number of crosslinkable groups increases, the modulus of the polymerised material generally also increases. The overall ratio of the crosslinking groups to non-crosslinking groups is important to obtaining a low modulus in this application more so than absolute values of n, m, o, p, q, s. Postcure extractables can be reduced by increasing the overall number of —Si—O-monomeric units; extractables are minimised by increasing the length of the macromonomers to obtain as high a molecular weight as viscosity constraints will allow (without increasing the overall amount of crosslinkable groups per unit length of polymer).

The invention will be further described by reference to the following non limiting examples.

EXAMPLE 1

This example illustrates the preparation of methacryloxypropyl terminated 1.2%-(poly-methylmethacryloxypropyl-siloxane) (dimethyl siloxane) copolymer.

Preparation of Stock Solutions:

A stock solution of tetramethyldisiloxane (IS) was prepared by dissolving 8.00 g of tetumethyldisiloxane in 353.08 g of octamethylcyclotetrasiloxane.

A stock solution of 1,3,5,7-tetramethylcyclotetrasiloxane (TMCTS) was prepared by dissolving 3.618 g of 1,3,5,7-tetramethylcyclotetrasiloxane in 46.2367 g of octamethylcyclotetrasiloxane.

Preparation of Copolymer Precursor:

5 g of the tetramethyldisiloxane stock solution, 5 g, of the 1,3,5,7-tetramethylcyclotetrasiloxane stock solution and 40.00 g of octamethylcyclotetrasiloxane were mixed in a round bottom flask under an inert atmosphere. To the mixture was added 50 mL of dry toluene followed by 0.125 g of trifluoromethanesulfonic acid. The reaction mixture was allowed to stir at room temperature for 3 days. 10.0 g of anhydrous sodium carbonate was then added and the mixture stirred overnight, before the sodium carbonate was filtered off. The toluene solution was poured into an excess of ethanol to precipitate the siloxane copolymer which was then transferred to a kugelrohr distillation apparatus and stripped of low molecular weight species to give the poly-methylhydrosiloxane-dimethylsiloxane copolymer as a clear colourless oil (viscosity 32000 cS. MW equivalent 83,000 AMU's, RI=1.4048).

19.06 g of the poly-methylhydrosiloxane-dimethylsiloxane copolymer so prepared was dissolved in 107 mL of dry toluene along with 3.26 g of allyl methacrylate. The reaction was initiated by the addition of 200 uL of 0.02M solution of $H_2PtCl_6$ in isopropanol and stirred for. 4 days at room temperature. Activated carbon is added and the mixture stirred for 3 hours before the carbon was filtered off and the solution passed through a 0.2 um Teflon filter. The IRGACURE 819 photoinitiator (30.5 mg) was then added before the solvent was removed under reduced pressure and the siloxane product heated to 40° C. on a kaglelrohr apparatus under vacuum overnight to give a clear yellow oil (Viscosity 24000 cS, MW equivalent 64,000 AMU's, RI=1.40668).

EXAMPLE 2

This example illustrates the physical properties of the cured crosslinkable siloxane macromolecule in Example 1. 0.4 mL of the siloxane macromolecule prepared in Example 1 was poured into a 20 mm diameter polypropylene mould and pressed flat with a polypropylene top plate. The sample was irradiated with 4 mW/cm-$^2$ blue light (wavelength range 420-460 nm) for 40 minutes to give a clear colourless disc. The shear modulus of the cured polymer was measured by MFR as being 27 kPa.

EXAMPLE 3

This example illustrates the preparation of acrylamide terminated 0.5%-(poly-acrylamide substituted siloxane) (dimethyl siloxane) copolymer 11.0 g of the TMDS stock solution mentioned in Example 1, 5.5555 g of the 1,3,5,7-TMCTS stock solution mentioned in Example 1 and 84.4445 g of octamethylcyclotetrasiloxane were mixed in a round bottom flask under an inert atmosphere. To the mixture was added 100 ml of dry toluene followed by 0.250 g of trifluoromethanesulfonic acid. The reaction mixture was allowed to stir at room temperature for 4 days. 20.0 g of anhydrous sodium carbonate was then added and the mixture stirred overnight, before the sodium carbonate was filtered off. The toluene solution was poured into an excess of ethanol to precipitate the siloxane copolymer which was then transferred to a kugelrohr distillation apparatus and stripped of low molecular weight species to give the poly-methylhydrosiloxane-dimethylsiloxane copolymer as a clear colourless oil (viscosity 30000 cS, MW 84000 AMU's, RI=1.4049).

19.791 g of the poly-methylhydrosiloxane-dimethylsiloxane copolymer prepared was dissolved in 75.7 ml of dry toluene along with 0.754 g of allyl alcohol. The reaction was initiated by the addition of 0.162 g of Karstedt's catalyst and stirred for 16 hours at 70° C. Upon cooling to room temperature activated carbon is added and the mixture stirred for 3 hours before the carbon was filtered off and the solution passed through a 0.2 um Teflon filter. Removal of the solvent under reduced pressure produced 18.980 g of poly-hydroxypropylmethylsiloxane-dimethylsiloxane copolymer. This was dissolved in 50 ml of dried and purified di-isopropyl ether along with 0.831 g azlactone and 159.7 ul DBU in a Young's vessel. The mixture was then vacuated and heated at 65° C. for 16 hours. The di-isopropyl ether solution was cooled to room temperature and poured into an excess of ethanol. The siloxane product was transferred to a kugelrohr apparatus and the solvent was removed under reduced pressure and the siloxane product heated to 40° C. on a kuglelrohr apparatus under reduced pressure overnight to give an acrylamide crosslinkable siloxane (having functional (ie -L-Z) groups of formula m below) as a clear colourless oil (viscosity 18000 cS, MW 97000 AMU's, RI=1.4068, Specific Gravity: 0.954 g mL$^{-1}$).

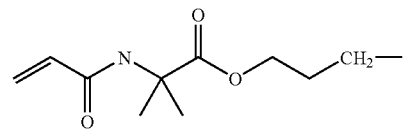

Formula III

The polymer was taken up in toluene, along with 0.3% IRG 651 by weight to polymer, and the toluene removed under reduced pressure to yield a photo-polymerisable polymer formulation.

EXAMPLE 4

This example illustrates the physical properties of the cured crosslinkable siloxane macromolecule in Example 3. 0.4 ml of the siloxane macromolecule prepared in Example 3 was poured into a 20 mm diameter polypropylene mould and pressed flat with a polypropylene top plate. The sample was irradiated with 4 mW/cm$^2$ UV light source (mercury vapour lamp) for 15 seconds to give a clear colourless disc. The shear modulus of the cured polymer was measured by MFR as being 4.6 kPa.

EXAMPLE 5

This example illustrates the preparation of methacryloxypropyl terminated 0.22%-(poly-methylmethacryloxypropylsiloxane) (dimethyl siloxane) copolymer. 10.0000 g of the TMDS stock solution of Example 1, 3.5000 g of the 1,3,5,7-TMCTS stock solution of Example 1 and 86.5000 of octamethylcyclotetrasiloxane were mixed in a round bottom flask under an inert atmosphere. To the mixture was added 50 ml of dry toluene followed by 0.250 g of trifluoromethanesulfonic acid. The reaction and workup conditions were executed as per Example 1 to give the. poly-methylhydrosiloxane-dimethylsiloxane copolymer as a clear colourless oil (viscosity 46000 cS, RI=1.40485).

19.5210 g of the 0.22 mol %-poly-methylhydrosiloxane-dimethylsiloxane copolymer was dissolved in 109.6 ml of dry toluene along with 3.3360 g of allyl methacrylate. The reaction was initiated by the addition of 202.1 ul of 0.02M solution of $H_2PtCl_6$ in isopropanol and stirred for 4 days at room temperature. Activated carbon is added and the mixture stirred for 3 hours before the carbon was filtered off and the solution passed through a 0.2 um Teflon filter. A visible initiator was introduced (IRGACURE 819, 58.6 mg) before the solvent was removed under reduced pressure and the siloxane product heated to 40° C. on a kuglelrohr apparatus under vacuum overnight to give a clear colourless oil. (Viscosity 73500 cS, MW 115000 AMU's, RI=1.4057, Specific gravity=0.941 g mL$^{-1}$)

EXAMPLE 6

This example illustrates the physical properties of the cured crosslinkable siloxane macromolecule in Example 5. 0.4 ml of the siloxane macromolecule prepared in Example 5 was poured into a 20 mm diameter polypropylene mould and pressed flat with a polypropylene top plate. The sample was irradiated 20 mW/cm$^2$ visible light source (mercury vapour lamp with appropriate filters to pass only >400 nm light) for 15 seconds to give a clear colourless disc. The shear modulus of the cured polymer was measured by MFR as being 1.5 kPa.

EXAMPLE 7

This example illustrates the preparation of hydride terminated methacryloxypropyl terminated 0.31%-(poly-methylmethacryloxypropylsiloxane) (dimethyl siloxane) copolymer. 10.0000 g of the tetramethyldisiloxane stock solution, 4.0000 g of the 1,3,5,7-tetramethylcyclotetrasiloxane stock solution, 86.0000 g of octamethylcyclotetrasiloxane, 50 ml of dry toluene and 0.250 g of trifluorometesufonic acid were reacted and worked up as in example 5. (viscosity 32000 cS, RI=1.4059).

18.6742 g of the 0.31 mol %-poly-methylhydrosiloxane-dimethylsiloxane copolymer prepared was dissolved in 104.8 ml of dry toluene along with 3.1913 g of allyl methacrylate and 193.3 ul of 0.02M solution of $H_2PtCl_6$ in isopropanol and reacted and worked up as in example 5. IRGACURE 651 photoinitiator (56.0 mg) was then added before the solvent was removed under reduced pressure and the siloxane product heated to 40° C. on a kuglelrohr apparatus under vacuum overnight to give a clear colourless oil. (viscosity 26500 cS, MW 110000 AMU's, RI=1.4049, Specific gravity=0.962 g mL$^{-1}$)

EXAMPLE 8

This example illustrate& the physical properties of the cured crosslinkable siloxane macromolecule in Example 7. 0.4 ml of the siloxane macromolecule prepared in Example 7 was poured into a 20 mm diameter polypropylene mould and pressed flat with a polypropylene top plate. The sample was irradiated UV light source (mercury vapour lamp) for 15 seconds to give a clear colourless disc. The shear modulus of the cured polymer was measured by MFR as being 0.3 kPa.

EXAMPLE 9

This example illustrates the preparation of methacryloxypropyl terminated 1.0%-(poly-methylmethacryloxypropylsiloxane) (dimethyl siloxane) copolymer of increased molecular weight. 2.8 g of the tetramethyldisiloxane stock solution, 4.0 g of the 1,3,5,7-tetramethylcyclotetrasiloxane stock solution, 34.4 g of octamethylcyclotetrasiloxane, 50 ml of dry toluene and 0.250 g of trifluoromethanesulfonic acid were reacted and worked up as in example 5. (viscosity 44000 cS, MW 117000 AMU's).

18.41 g of the 1.0 mol %-poly-methylhydrosiloxane-dimethylsiloxane copolymer prepared was dissolved in 100 ml of dry toluene along with 3.15 g of allyl methacrylate and 190 ul of 0.02M solution of $H_2PtCl_6$ in isopropanol and reacted and worked up as in example 5. IRGACURE 651 photoinitiator (55 mg) was then added before the solvent was removed under reduced pressume and the siloxane product heated to 40° C. on a kuglelrohr apparatus under vacuum overnight to give a clear colourless oil. (viscosity 110000 cS, MW 200000 AMU's, RI=1.4080, Specific gravity=0.937 g mL$^{-1}$)

EXAMPLE 10

This example illustrates the physical properties of the cured crosslinkable siloxane macromolecule in Example 10. 0.4 ml of the siloxane macromolecule prepared in Example 10 was poured into a 20 mm diameter polypropylene mould and pressed flat with a polypropylene top plate. The sample was irradiated UV light source (mercury vapour lamp) for 60 seconds to give a clear colourless disc. The shear modulus of the cured polymer was measured by MFR as being 5.0 kPa.

EXAMPLE 11

This example illustrates the ability of the polymers to be autoclaved. 3.0 g of the methacryloxypropyl terminated 0.22%-(poly-methylmethacryloxypropylsiloxane) (dimethyl siloxane) copolymer prepared in Example 9 was transferred to a glass syringe and autoclaved. 0.4 ml of the autoclaved siloxane was poured into a 20 mm diameter polypropylene mould and pressed flat with a polypropylene top plate. The sample was irradiated 20 mW/cm-$^2$ visible light source (xenon lamp) for 5 minutes to give a clear colourless disc. The shear modulus of the cured polymer was measured by OR as being 4.0 kPa.

EXAMPLE 12

This example illustrates the preparation of vinyl terminated (0.91 mol % poly-methylhydrosiloxane) (4 mol % poly-diphenylsiloxane) (dimethyl siloxane) copolymer. The copolymer precursor was prepared as follows. 30.2670 g of the poly(dimethylsiloxane-co-diphenylsiloxane), divinyl terminated [1,000 cS, 15 wt % diphenylsiloxane, Mn ~18 900 (Aldrich)], 5.0 g of the TMCTS stock solution outlined in Example 1, and 59.733 g of octamethylcyclotetrasiloxane were mixed in a round bottom flask under an inert atmosphere. To the mixture was added 100 ml of dry toluene followed by 0.250 g of trifluoromethanesulfonic acid. The mixture was reacted and worked up as in example 5 to give the divinyl terminated copolymer as a clear colourless oil (viscosity 9 550 cS, MW equivalent 43,700 AMU's).

17.7312 g of the poly-methylhydrosiloxanedimethylsiloxane-diphenylsiloxane, divinyl terminated copolymer prepared was dissolved in 99.5 ml of dry toluene along with 6.0603 g of allyl methacrylate. The reaction was initiated by the addition of 183.5 ul of 0.02M solution of $H_2PtCl_6$ in isopropanol and stired for 4 days at room temperature. Activated carbon is added and the mixture stirred for 3 hours before the carbon was filtered off and the solution passed through a 0.2 um Teflon filter. The IRGACURE 819 photoinitiator (28.4 mg) was then added before the solvent was removed under reduced pressure and the siloxane product heated to 40° C. on a kuglelrohr apparatus under vacuum overnight to give a clear oil. (viscosity 75000 cS, MW 220000 AMU's, RI=1.43)

EXAMPLE 13

This example illustrates the physical properties of the cured crosslinkable siloxane macromolecule in Example 12. 0.4 ml of the siloxane macromolecule prepared in Example 12 was poured into a 20 mm diameter polypropylene mould and pressed flat with a polypropylene top plate. The sample was irradiated with 20 mW/cm-$^2$ visible light source(xenon lamp) for 45 seconds to give a clear colourless disc. The shear modulus of the-cured polymer was measured by MFR as being 7.0 kPa.

Those skilled in the art will appreciate that the invention described herein is susceptible to variations and modifications other than those specifically described. It will be understood that the present invention encompasses all such variations and modifications that fall within the spirit and scope.

The invention claimed is:

1. A biomedical implant comprising a polymer that is cured from a composition comprising a random or block macromonomer of general formula:

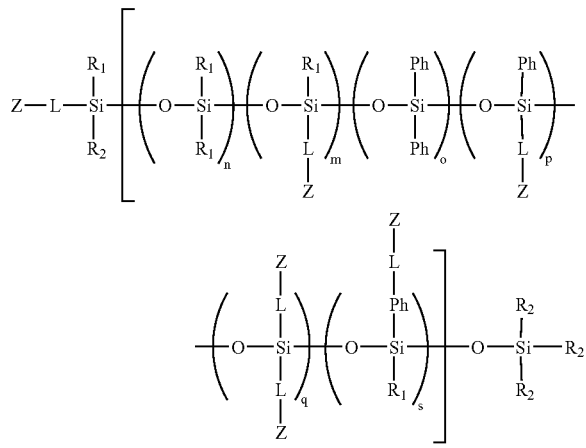

wherein

L is a spacer group;

Z is a crosslinkable group and the macromonomer contains at least one pendant Z;

each $R_1$ is independently $C_1$ to $C_6$ alkyl or perfluorinated $C_1$ to $C_6$ alkyl;

each $R_2$ is independently an $R_1$ or L-Z group; the molar percentage of:

n is from 50 up to but not including 100%;

m is from 0 to 10%;

o is from 0 to 50%;

p is from 0 to 2%, and o+p=0 when L or $R_1$ contain fluorine;

q is from 0 to 2%;

s is from 0 to 2%;

the molecular weight of the macromonomer being more than 3,000; and wherein the macromonomer is curable in vivo and when polymerized to form the cured polymer, the polymer has a shear modulus as measured by a Micro Fourier Rheometer between 0.1 and 5 kPa.

2. The biomedical implant according to claim 1 in which both terminal Si residues are bound to identical or different L-Z groups.

3. The biomedical implant according to claim 1 in which Z is an acryl or substituted acryl, methacryl or functional analogue of (meth)acryl capable of undergoing crosslinking reactions with a photoinitiator.

4. The biomedical implant according to claim 1 in which Z is an isocyanate or epoxy group.

5. The biomedical implant according to claim 1 in which L is a linear, branched or cyclic hydrocarbon chain, optionally including hetero atoms, or carbonyl.

6. The biomedical implant according to claim 1 in which m is from 0 up to 5% and o is from 0 up to 25%.

7. The biomedical implant according to claim 1 in which the total molar percentage of m+p+q+s is less than 1%.

8. The biomedical implant according to claim 1 including di-aromatic substitutions along the backbone or perfluorinated alkyl substitutions on the backbone.

9. The biomedical implant according to claim 1 wherein the macromonomer has a molecular weight of between 60,000 and 160,000.

10. The biomedical implant of claim 1, wherein the implant is an intraocular lens.

11. The biomedical implant of claim 1, wherein the implant is a breast implant.

12. The biomedical implant of claim 1, wherein the implant is a soft tissue replacement.

13. The biomedical implant of claim 1, wherein the implant is a soft tissue filling agent.

14. The biomedical implant of claim 1, wherein the implant is a vitreous/aqueous humor replacement.

15. The biomedical implant of claim 1, wherein the composition has a viscosity of 1,000-60,000 cS at 25° C. and the polymer comprises at least 80% of the macromonomer by weight.

* * * * *

UNITED STATES PATENT AND TRADEMARK OFFICE
CERTIFICATE OF CORRECTION

| | |
|---|---|
| PATENT NO. | : 7,452,377 B2 |
| APPLICATION NO. | : 10/523349 |
| DATED | : November 18, 2008 |
| INVENTOR(S) | : Jason Watling et al. |

It is certified that error appears in the above-identified patent and that said Letters Patent is hereby corrected as shown below:

Column 14, line 12, delete "OR" and substitute therefore --MFR--.

Signed and Sealed this

Thirty-first Day of March, 2009

JOHN DOLL
*Acting Director of the United States Patent and Trademark Office*